US011083365B2

(12) United States Patent
Kim et al.

(10) Patent No.: US 11,083,365 B2
(45) Date of Patent: Aug. 10, 2021

(54) LOOP ANTENNA MODULE FOR CAPSULE-TYPE ENDOSCOPE AND CAPSULE-TYPE ENDOSCOPE INCLUDING THE SAME

(71) Applicant: Industry-Academic Cooperation Foundation, Chosun University, Gwangju (KR)

(72) Inventors: Youn Tae Kim, Daejeon (KR); Se Woong Kim, Gwangju (KR); Jong Jin Baek, Jeollanam-do (KR)

(73) Assignee: Industry-Academic Cooperation Foundation, Chosun University, Gwangju (KR)

( * ) Notice: Subject to any disclaimer, the term of this patent is extended or adjusted under 35 U.S.C. 154(b) by 855 days.

(21) Appl. No.: 15/848,046

(22) Filed: Dec. 20, 2017

(65) Prior Publication Data
US 2018/0235449 A1 Aug. 23, 2018

(30) Foreign Application Priority Data
Feb. 17, 2017 (KR) .................. 10-2017-0021777

(51) Int. Cl.
*A61B 1/04* (2006.01)
*A61B 1/00* (2006.01)
(Continued)

(52) U.S. Cl.
CPC .......... *A61B 1/041* (2013.01); *A61B 1/00016* (2013.01); *A61B 1/051* (2013.01);
(Continued)

(58) Field of Classification Search
CPC ....... A61B 1/041; A61B 5/0015; A61B 1/051; A61B 1/00016; A61B 5/073;
(Continued)

(56) References Cited

U.S. PATENT DOCUMENTS

2006/0043198 A1* 3/2006 Forster ............ G06K 19/07756
235/492
2008/0249360 A1 10/2008 Li et al.
(Continued)

FOREIGN PATENT DOCUMENTS

| DE | 102011011638 A1 | * | 8/2012 | ......... G02B 23/2484 |
| GB | 201612175 | * | 8/2016 | ........... A61B 5/0031 |
| KR | 10-2007-0018858 A | | 2/2007 | |

OTHER PUBLICATIONS

The University of Rhode Island, Calculating the Resistance of a Wire, 2016, p. 1 (Year: 2016).*
(Continued)

*Primary Examiner* — Michael J Carey
*Assistant Examiner* — Christen Hicks
(74) *Attorney, Agent, or Firm* — Renner, Otto, Boisselle & Sklar, LLP

(57) ABSTRACT

A loop antenna module used in a capsule-type endoscope comprises: a feed portion substrate including a pair of coupling pads provided on a surface; and a loop antenna body including a loop antenna substrate coupled to the feed portion substrate, a pair of coupling pads provided on a surface of the loop antenna substrate and capacitively coupled to a further pair of coupling pads provided in the feed portion substrate, and a conductive wire extended from the pair of coupling pads provided on the surface of the loop antenna substrate to have a spiral pattern, wherein the loop antenna substrate, the pair of coupling pads and the conductive wire provided in the loop antenna substrate are formed of a transparent material.

16 Claims, 1 Drawing Sheet

(51) Int. Cl.
*A61B 5/07* (2006.01)
*A61B 5/00* (2006.01)
*A61B 1/05* (2006.01)
*G02B 23/24* (2006.01)

(52) U.S. Cl.
CPC ............ *A61B 5/0015* (2013.01); *A61B 5/073* (2013.01); *A61B 1/00009* (2013.01); *A61B 1/00025* (2013.01); *A61B 1/00112* (2013.01); *A61B 2560/0214* (2013.01); *G02B 23/2484* (2013.01)

(58) Field of Classification Search
CPC ........ A61B 2560/0214; A61B 1/00009; A61B 1/00112; A61B 1/00025; A61B 1/00064; G02B 23/2484; H01Q 1/24; H01Q 7/00
USPC ........................................................ 600/109
See application file for complete search history.

(56) References Cited

U.S. PATENT DOCUMENTS

2009/0281381 A1* 11/2009 Takenaka ................ A61B 1/041
600/109
2009/0304093 A1* 12/2009 Shim .................... H04B 13/005
375/259
2012/0071710 A1* 3/2012 Gazdzinski .......... A61B 1/0002
600/101

OTHER PUBLICATIONS

Poole et al., Microwave Active Circuit Analysis and Design, 2015, Elsevier, p. 73 (Year: 2015).*

* cited by examiner

LOOP ANTENNA MODULE FOR CAPSULE-TYPE ENDOSCOPE AND CAPSULE-TYPE ENDOSCOPE INCLUDING THE SAME

CROSS-REFERENCE TO RELATED APPLICATION

This application claims the benefit of priority to Korean Patent Application No. 10-2017-0021777, filed on Feb. 17, 2017 with the Korean Intellectual Property Office, the entirety of which is incorporated herein by reference.

BACKGROUND

The present disclosure relates to a loop antenna module used for a capsule-type endoscope, as well as a capsule-type endoscope including the same.

The present disclosure has been derived from research [Assignment Management number: 1711039653, title: In-body channel research for human body communications and power transmission for implant devices] conducted as part of a personal research support project by the Ministry of Science, ICT, and the Future Planning and National Research Foundation of Korea.

Capsule-type endoscopes are medical devices used to examine the internal organs of the body. In a case in which patients swallow capsule-type endoscopes like a pill, capsule-type endoscopes move from the oral cavity to the rectum, while capturing images of internal organs, such as the stomach, the small intestine, and the large intestine, and may be excreted from the human body.

Images captured by a camera provided in capsule-type endoscopes are wirelessly transmitted to an image storage device worn on the body of a patient. The images transmitted during an inspection period may be continuously stored in an image storage device. After the inspection is completed, doctors may use the images stored in the image storage device to diagnose the health condition of patients. In terms of the use of capsule-type endoscopes, there is none of the pain and discomfort associated with general endoscopy. Capsule-type endoscopes may also obtain images of the small intestine, unable to be reached by general endoscopy.

Such capsule-type endoscopes, as described above, may include a camera capturing images of internal organs, a light source irradiating light to internal organs when images are captured, a wireless transmitter and an antenna, wirelessly transmitting the captured images to an image storage device on the exterior of the body, and a battery supplying power required to operate endoscopes, in a capsule having a size similar to that of a large pill.

When light is emitted from a light source to irradiate light to internal organs, a camera may capture images of internal organs. In general, a camera may capture one to three images per second. Wireless transmitters may modulate video signals, in order to wirelessly transmit captured images. Subsequently, modulated signals may be emitted as radio signals through an antenna to be transmitted to an image storage device disposed on the exterior of the body. Batteries may supply power required for the operation of cameras, light sources, and wireless transmitters.

Antennas used in capsule-type endoscopes of the related art have been disposed on an opposite side of an endoscope to a camera and a light source, since, in a case in which antennas are disposed directly in front of a camera and a light source, light emitted by a light source and the visual field of a camera may be blocked by antennas.

In detail, in order to accurately diagnose diseases through captured images, images of internal organs are required to be captured at various angles. To this end, pairs of a camera and a light source needed to be disposed on opposing ends of capsule-type endoscopes.

To this end, antennas may be disposed on the capsule surface of capsule-type endoscopes using a planar antenna technique. For example, microstrip line antennas may be disposed on the body surface of capsule-type endoscopes. In this case, an antenna forming technique of bending a microstrip line may be used, in order to allow an antenna to be disposed on the body surface thereof, having a relatively small area. In order to allow a microstrip line antenna to be disposed on the surface of capsule-type endoscopes, a special manufacturing process is required, since, in a case in which a copper wire forming a microstrip line is in direct contact with internal organs, a copper wire may harm internal organs, while body fluids having a relatively high acid level, such as gastric juice, may corrode a copper wire. The surface of antennas should be coated with a special material to prevent interaction with internal organs. Accordingly, there are problems in which the manufacturing process of capsule-type endoscopes may be complicated, and manufacturing costs may be increased.

Instead of providing antennas on the surface of capsule-type endoscopes, a technique of miniaturizing an antenna to be disposed in a space between a camera and a light source may be used. For example, coil antennas may be used. A ferromagnetic core, such as ferrite, may be inserted into the central portion of a coil, so that coil antennas may have a size small enough to be disposed in a narrow space between a camera and a light source. However, such small antennas may have relatively low radiation efficiency.

Since radiation efficiency, a ratio of power input to an antenna to radiated power, is generally proportional to the size of an antenna, radiation efficiency may be decreased in a case in which an antenna is miniaturized. The intensity of radio waves radiated from an antenna may be reduced, due to lowered radiation efficiency. As a result, there may be a problem in which image storage devices disposed on the exterior of the body may not properly receive video signals transmitted by capsule-type endoscopes.

SUMMARY

An aspect of the present disclosure provides a loop antenna module preventing light emitted from a light source and a visual field of a camera from being blocked by an antenna, feeding a signal to the loop antenna, even in the case in which a loop antenna body is not physically connected to a feed portion substrate, thereby allowing a loop antenna to be easily manufactured and disposed and allowing for impedance matching even without a separate matching element.

In addition, another aspect of the present disclosure provides a capsule-type endoscope capturing an image of an internal organ at various angles.

According to a first aspect of the present disclosure, a loop antenna module, comprises: a feed portion substrate including a pair of coupling pads provided on a surface; and a loop antenna body including a loop antenna substrate coupled to the feed portion substrate, a pair of coupling pads provided on a surface of the loop antenna substrate and capacitively coupled to a further pair of coupling pads provided in the feed portion substrate, and a conductive wire extended from the pair of coupling pads provided on the surface of the loop antenna substrate to have a spiral pattern. The loop antenna module is used in a capsule-type endoscope in which the loop antenna substrate, the pair of coupling pads provided in the loop antenna substrate, and the conductive wire are formed of a transparent material.

According to a second aspect of the present disclosure, a capsule-type endoscope comprising: a camera; a light source; a battery; and loop antenna modules equipped at both ends of the battery, wherein each of the loop antenna modules includes: a feed portion substrate including a pair of coupling pads, the camera and the light source provided on a surface; and a loop antenna body including a loop antenna substrate coupled to the feed portion substrate having a camera through-hole formed in a central portion of the loop antenna substrate, having the camera inserted into the central portion, and a light source hole having the light source inserted into the light source hole, disposed on a periphery of the camera through-hole, a pair of coupling pads provided on a surface of the loop antenna substrate and capacitively coupled to a further pair of coupling pads provided in the feed portion substrate, and a conductive wire extended from the pair of coupling pads provided on the surface of the loop antenna substrate to have a spiral pattern. A pair of coupling pads, the conductive wire, and the loop antenna substrate, provided in the loop antenna body, are formed using a transparent material.

BRIEF DESCRIPTION OF DRAWINGS

The above and other aspects, features, and advantages of the present disclosure will be more clearly understood from the following detailed description when taken in conjunction with the accompanying drawings, in which.

DETAILED DESCRIPTION

Hereinafter, exemplary embodiments in the present disclosure will be described as follows with reference to the attached drawings.

The present disclosure may, however, be exemplified in many different forms and should not be construed as being limited to the specific embodiments set forth herein. Rather, these embodiments are provided so that this disclosure will be thorough and complete, and will fully convey the scope of the disclosure to those skilled in the art.

The contents of the present disclosure described below may have a variety of configurations, and only a required configuration is proposed herein, but the present disclosure is not limited thereto.

Figure 1:
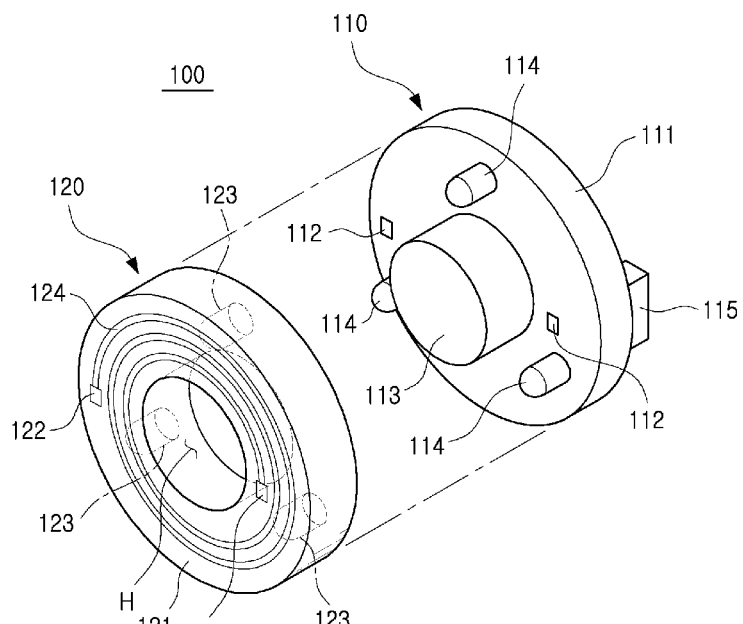
FIG. 1 is a view of a loop antenna module used in a capsule-type endoscope according to an exemplary embodiment in the present disclosure.

FIG. 1 is a view of a loop antenna module 100 used in a capsule-type endoscope according to an exemplary embodiment in the present disclosure.

As illustrated in FIG. 1, the loop antenna module 100 according to an exemplary embodiment may include a power feeding module 110 supplying a signal to a loop antenna body 120 and a loop antenna body 120 transmitting a signal received from the power feeding module 110. An operating frequency of the loop antenna module 100 described above may be provided as a frequency of an industrial, scientific, and medical (ISM) band (e.g., 2.0 GHz or higher) usable in a medical device.

In detail, the power feeding module 110 may include a feed portion substrate 111 having a cylindrical shape (or a disk shape), as well as a pair of coupling pads 112, a camera 113, and a light source 114, provided on one surface of the feed portion substrate 111.

The pair of coupling pads 112 of the power feeding substrate 111 may be provided in positions opposing each other across the camera 113. A balun 115 converting a signal output from a wireless transmission-reception module (not illustrated) into a signal having a phase difference of 180 degrees to be transmitted to the pair of coupling pads 112 provided in the power feeding substrate 111 may be provided on the other surface of the power feeding substrate 111.

The loop antenna body 120 may include a loop antenna substrate 121 coupled to the feed portion substrate 111 described above, the pair of coupling pads 122 provided on surface of a loop antenna substrate 121 and capacitively coupled to the pair of coupling pads 112 provided in the feed portion substrate 111, and a conductive wire 124 extended from the further pair of coupling pads 122 provided on the surface of the loop antenna substrate 121 to have a spiral pattern. The loop antenna substrate 121 described above may have a cylindrical shape (or a disc shape) in the same manner as the feed portion substrate 111.

The loop antenna substrate 121, as well as the further pair of coupling pads 122 and the conductive wire 124, described above, provided in the loop antenna substrate 121 may be formed using a transparent material. For example, a transparent electrode having conductivity, formed, for example, from a material such as indium tin oxide (ITO), fluorine-doped tin oxide (FTO), and silver coated polyester file (AgHT), may be used as the further pair of coupling pads 122 and the conductive wire 124.

In addition, a non-conductive material formed using a transparent material, such as glass, may be used as the loop antenna substrate 121.

In other words, according to an exemplary embodiment, the loop antenna substrate 121, as well as the further pair of coupling pads 122 and the conductive wire 124, provided in the loop antenna substrate 121, may be formed using a transparent material, thereby preventing light emitted from the light source 114 and a visual field of the camera 113 from being blocked by the loop antenna module 120.

A camera through-hole H into which a camera 113 is inserted may be formed in a central portion of the loop antenna substrate 121. A light source hole 123, into which the light source 114 is inserted may be formed on a periphery of the camera through-hole H. When the feed portion substrate 111 is coupled to the loop antenna substrate 121, the camera 113 may be inserted into the camera through-hole H, and the light source 114 may be inserted into the light source hole 123. The light source hole 123 may be formed to protrude further forward and may be formed to correspond to a number of and a position of the light sources 114.

The pair of coupling pads 112 provided in the power feeding substrate 111 and the further pair of coupling pads (122) provided in the loop antenna substrate 121, described above, may be formed to oppose each other, when the power feeding substrate 111 is coupled to the loop antenna substrate 121.

The loop antenna module 100, described above, may be operated as follows.

In other words, in a case in which a signal is input to the balun 115, the signal having been input may be divided into two signals having a phase difference of 180 degrees to be input to a coupling pad 112 provided in the feed portion substrate 111.

In a case in which the loop antenna body 120 is coupled to the feed portion substrate 111, the pair of coupling pads 112 of the feed portion substrate 111 may be formed to oppose the further pair of coupling pads 122 of the loop antenna body 120 across the feed portion substrate 111. Two coupling pads 112 and 122 may be capacitively coupled to each other.

Thus, a signal input to the pair of coupling pads 112 of the feed portion substrate 111 may be transmitted to the further pair of coupling pads 122 provided in the loop antenna body 120. The signal transmitted to the further pair of coupling pads 122 provided in the loop antenna body 120 may flow along the conductive wire 124. Since the conductive wire 124 has a coil form, the signal flowing along the conductive wire 124 may be transmitted as a radio signal.

On the other hand, the conductive wire 124 provided in the loop antenna body 120 may have resistance corresponding to the sum of radiation resistance and conductive resistance. The radiation resistance is provided as resistance representing power of a radio wave radiated from the conductive wire 124. In the case of a loop antenna, the radiation resistance is expressed as Formula 1 below.

$$R_r = \left(\frac{177 \cdot N \cdot A}{\lambda^2}\right)^2 \quad \text{[Formula 1]}$$

Here, Rr refers to radiation resistance, N refers to a turns number of a conductive wire, A refers to an area of the loop antenna formed by the conductive wire 124, and λ refers to a wavelength of a frequency at which the loop antenna is operated.

In the meantime, the conductive resistance is provided as resistance occurring due to conductivity of the conductive wire 124 and is known for being expressed as Formula 2 below, according to the definition of conductivity.

$$R_c = \frac{1}{\sigma} \cdot \frac{l}{A} \quad \text{[Formula 2]}$$

Here, Rc refers to conductive resistance, σ refers to conductivity, l refers to a length of the conductive wire 124, and A refers to a cross-sectional area of the conductive wire 124.

A capsule-type endoscope may have a relatively small size, so that a patient may easily swallow the capsule endoscope, and currently commercialized capsule endoscopes have a diameter of about 1 cm. Thus, a diameter of the loop antenna formed by the conductive wire 124 of the loop antenna module 100 for capsule-type endoscope of an exemplary embodiment may be a maximum of 1 cm. In a case in which a turns number of the conductive wire 124 is 1, the diameter of the loop antenna formed by the conductive wire 124 is 1 cm, and an operating frequency of the loop antenna module 100 is 2.4 GHz, the radiation resistance may have about 0.8 ohms of resistance, according to Formula 1 described above.

As described in Formula 1, in order to increase power of a radio wave radiated from the loop antenna module 100, a turns number N of the conductive wire 124 should be increased, but the diameter of the loop antenna formed by the conductive wire 124 may be limited. Thus, in order to increase the turns number of the conductive wire 124, a width of the conductive wire 124 should be reduced. As the width of the conductive wire 124 is decreased, a cross-sectional area A of the conductive wire 124 may also be reduced, thereby increasing conductive resistance Rc of the conductive wire 124 (see Formula 2).

In other words, given that the diameter of the loop antenna formed by the conductive wire 124 is limited (thus, an area of the loop antenna formed by the conductive wire 124 is also limited), as the turns number of the conductive wire 124 is increased, an entirety of radiation resistance Rr and conductive resistance Rc is increased. Maximum power may be transmitted through impedance matching using characteristics described above.

In other words, the turns number of the conductive wire 124 may be increased, thereby increasing the conductive resistance of the conductive wire 124. In addition, the turns number may be adjusted to be closer to a real part (in general, 50 ohms) of impedance in a direction from the further pair of coupling pads 122 toward the feed portion substrate 111, thereby matching impedance. In other words, the cross-sectional area of the conductive wire 124 may be reduced, and a length thereof may be increased, so that the turns number of the conductive wire 124 may be increased in a limited area of the loop antenna.

In the meantime, since the conductive wire 124 is provided in the loop antenna substrate 121 to have a spiral pattern, the conductive wire 124 may have an inductance component. The inductance component of the conductive wire 124 should be offset so that input impedance of the loop antenna formed by the conductive wire 124 may match impedance on a side of the feed portion substrate 111. According to an exemplary embodiment, capacitive coupling occurring between a further coupling pad 122 provided in the loop antenna body 120 and a coupling pad 112 provided in the feed portion substrate 111 may be used to offset the inductance component of the conductive wire 124.

In other words, a capacitance component is generated between the coupling pad 122 provided in the loop antenna body 120 and the coupling pad 112 provided in the feed portion substrate 111. In this case, the inductance component of the conductive wire 124 may be offset by allowing a size of the capacitance component to be equal to a size of the inductance component of the conductive wire 124, thereby achieving impedance matching.

The capacitance component described above may be determined by a size of respective coupling pads 122 and 112, a thickness of the loop antenna substrate 121, and a dielectric constant. The capacitance component may be set to have a desired value by adjusting a size of each item. The pair of coupling pads 112 and the further pair of coupling pads 122 may be formed to oppose each other when the feed portion substrate 111 is coupled to the loop antenna substrate 121 so that a level of capacitance may be easily adjusted. Such an impedance matching method may facilitate the manufacturing of the loop antenna.

In other words, a signal may be fed to the conductive wire 124 of the loop antenna through capacitive coupling between the pair of coupling pads 112 provided in the feed portion substrate 111 and the further pair of coupling pads 122 provided in the loop antenna substrate 121. Thus, the loop antenna substrate 121 is not required to be connected to the power feeding substrate 111. Thus, the loop antenna substrate 121 may be easily manufactured using a material different from the feed portion substrate 111.

Figure 2:
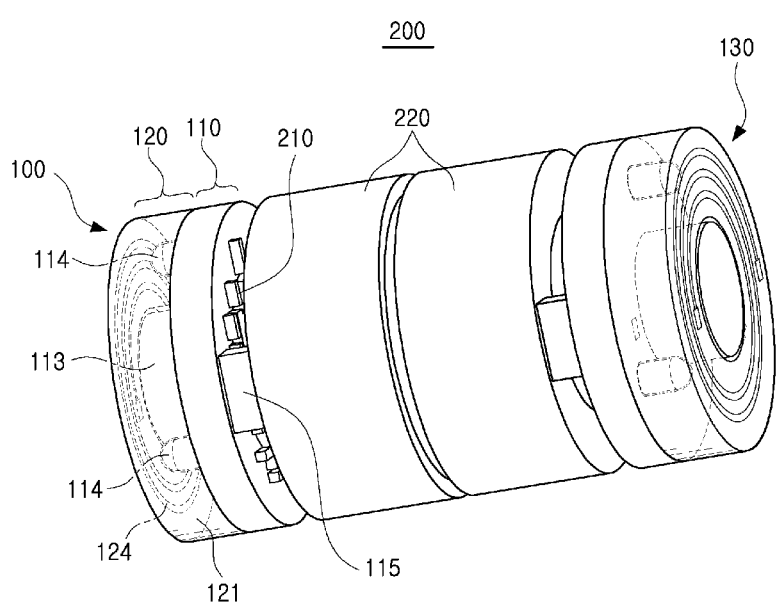
FIG. 2 is a view of a capsule-type endoscope to which a loop antenna module is applied according to an exemplary embodiment in the present disclosure.

FIG. 2 illustrates a capsule-type endoscope 200 to which loop antenna modules 100 and 130 according to an exemplary embodiment are applied.

As illustrated in FIG. 2, the capsule-type endoscope 200 may include the loop antenna modules 100 and 130 on opposing end portions of a battery 220. Two loop antenna modules 100 and 130 have the same structure as that illustrated in FIG. 1. Thus, a single loop antenna module 100 was marked using a reference numeral. The battery 220 may be the same as a button-type battery as illustrated in FIG. 2.

In addition, a wireless transmission-reception module 210, as well as a balun 115, may be further provided on the other surface of a feed portion substrate of a power feeding module 110. The wireless transmission-reception module 210 may process an image captured by a camera 113 to be converted into a signal appropriate for being wirelessly transmitted, and a converted signal may be transmitted to the balun 115.

As described above, according to an exemplary embodiment, the loop antenna substrate, as well as a pair of coupling pads and a conductive wire, provided in the loop antenna substrate, may be formed using a transparent material, thereby preventing light emitted from a light source and a visual field of the camera from being blocked by an antenna.

According to another exemplary embodiment, a level of capacitance, generated by capacitive coupling, between the pair of coupling pads provided in the feed portion substrate and the pair of coupling pads provided in the loop antenna body and a diameter, as well as a length of the conductive wire, may be set, in order to allow for impedance matching, thereby transmitting maximum power.

According to another exemplary embodiment, respective loop antenna modules may be provided on opposing end portions of a battery, thereby capturing an image of an internal organ at various angles.

As set forth above, according to exemplary embodiments in the present disclosure, a loop antenna substrate, as well as a pair of coupling pads and a conductive wire, provided in the loop antenna substrate, may be formed using a transparent material, so that light emitted from a light source and a visual field of a camera may not blocked by an antenna.

According to another exemplary embodiment in the present disclosure, a loop antenna body may be capacitively coupled to a feed portion substrate, so that a signal may be fed to a loop antenna even in the case in which the loop antenna body is not physically connected to the feed portion substrate. Thus, it is easy to manufacture and install the loop antenna.

In addition, according to another exemplary embodiment in the present disclosure, impedance matching is possible using capacitance and resistance of a conductive wire, generated by capacitive coupling without a separate matching element.

According to another exemplary embodiment in the present disclosure, respective loop antenna modules may be disposed on opposing end portions of a battery, thereby capturing an image of internal organs at various angles.

While exemplary embodiments have been shown and described above, it will be apparent to those skilled in the art that modifications and variations could be made without departing from the scope of the present invention as defined by the appended claims.

What is claimed is:

1. A loop antenna module for use in a capsule-type endoscope, comprising:

a feed portion substrate including a pair of coupling pads provided on a surface; and a loop antenna body including a loop antenna substrate coupled to the feed portion substrate, a pair of coupling pads provided on a surface of the loop antenna substrate and capacitively coupled to a further pair of coupling pads provided in the feed portion substrate, and a conductive wire extended from the pair of coupling pads provided on the surface of the loop antenna substrate to have a spiral pattern, wherein the loop antenna substrate, the pair of coupling pads and the conductive wire provided in the loop antenna substrate are formed of a transparent material; and wherein the pair of coupling pads provided on the surface of the feed portion substrate is configured for capacitive coupling with the pair of coupling pads provided on the surface of the loop antenna substrate for impedance matching.

2. The loop antenna module of claim 1, wherein the conductive wire and a pair of coupling pads provided in the loop antenna body are formed of a transparent electrode having conductivity, and the loop antenna substrate is formed of a non-conductive material.

3. The loop antenna module of claim 1, wherein a level of capacitance, generated by capacitive coupling, between a pair of coupling pads provided in the loop antenna body and the further pair of coupling pads provided in the feed portion substrate is equal to a level of inductance of the conductive wire for impedance matching.

4. The loop antenna module of claim 3, wherein the level of capacitance is adjustable by a size of respective coupling pads provided in the feeding portion substrate and the loop antenna body, a thickness of the loop antenna substrate, and a dielectric constant of the loop antenna substrate.

5. The loop antenna module of claim 3, wherein the impedance matching is possible by adjusting a cross-sectional area of and a length of the conductive wire.

6. The loop antenna module of claim 1, wherein the pair of coupling pads provided in the loop antenna substrate and the further pair of coupling pads provided in the feed portion substrate are formed to oppose each other, when the feed portion substrate is coupled to the loop antenna substrate.

7. The loop antenna module of claim 1, wherein, between opposing surfaces of the feed portion substrate, on an opposite surface of a surface on which the further pair of coupling pads is provided, a balun sending a signal to the further pair of coupling pads provided on the surface of the feeding portion substrate is provided.

8. The loop antenna module of claim 1, wherein an operating frequency of the loop antenna module is provided as a frequency of an industrial, scientific, and medical (ISM) band.

9. A capsule-type endoscope comprising:

a camera;
a light source;
a battery; and
loop antenna modules equipped at both ends of the battery, wherein each of the loop antenna modules includes:
a feed portion substrate including a pair of coupling pads, the camera and the light source provided on a surface; and a loop antenna body including a loop antenna substrate coupled to the feed portion substrate having a camera through-hole formed in a central portion of the loop antenna substrate, having the camera inserted into the central portion, and a light source hole having the light source inserted into the light source hole, disposed on a periphery of the camera through-hole, a pair of coupling pads provided on a surface of the loop antenna substrate and capacitively coupled to a further pair of coupling pads provided in the feed portion substrate, and a conductive wire extended from the pair of coupling pads provided on the surface of the loop antenna substrate to have a spiral pattern, wherein a pair of coupling pads, the conductive wire, and the loop antenna substrate, provided in the loop antenna body, are formed using a transparent material, and wherein the pair of coupling pads provided on the surface of the feed portion substrate is configured for capacitive coupling with the pair of coupling pads provided on the surface of the loop antenna substrate for impedance matching.

10. The capsule-type endoscope of claim 9, wherein the pair of coupling pads and the conductive wire provided in the loop antenna body are formed using a transparent electrode having conductivity, and the loop antenna substrate is a nonconductor.

11. The capsule-type endoscope of claim 9, wherein a level of capacitance, generated by capacitive coupling, between the pair of coupling pads provided in the loop antenna body and the further pair of coupling pads provided in the feed portion substrate is equal to a level of inductance of the conductive wire for impedance matching.

12. The capsule-type endoscope of claim 11, wherein the level of capacitance is adjustable by a size of respective coupling pads provided in the feed portion substrate and the loop antenna body, a thickness of the loop antenna substrate, and a dielectric constant of the loop antenna substrate.

13. The capsule-type endoscope of claim 11, wherein a cross-sectional area and a length of the conductive wire are adjustable for the impedance matching.

14. The capsule-type endoscope of claim 9, wherein the pair of coupling pads provided in the loop antenna substrate and the further pair of coupling pads provided in the feed portion substrate are formed to oppose each other, when the feed portion substrate is coupled to the loop antenna substrate.

15. The capsule-type endoscope of claim 9, wherein, between opposing surfaces of the feed portion substrate, on an opposite surface of a surface on which the further pair of coupling pads are provided, a balun transmitting a signal to the further pair of coupling pads provided on the surface of the feed portion substrate is provided.

16. The capsule-type endoscope of claim 9, wherein an operating frequency of the loop antenna module is provided as a frequency of an industrial, scientific, and medical (ISM) band.

* * * * *